United States Patent
Yang et al.

(10) Patent No.: US 12,403,125 B2
(45) Date of Patent: Sep. 2, 2025

(54) USE OF OVATODIOLIDE AGAINST SARS-CoV-2

(71) Applicants: Peking University Shenzhen Graduate School, Shenzhen (CN); CNS Biotek Corp., Taichung (TW); Gansu Evergreen Pharmaceuticals, Co., Ltd., Lanzhou (CN)

(72) Inventors: Zhen Yang, Shenzhen (CN); Yew-Min Tzeng, Taitung (TW); Linqi Zhang, Beijing (CN); Junmin Quan, Shenzhen (CN); Qing Chang, Lanzhou (CN); Qi Zhang, Beijing (CN); Chien-Ming Lee, Taitung (TW)

(73) Assignees: Peking University Shenzhen Graduate School, Shenzhen (CN); CNS Biotek Corp, Taichung (TW); Gansu Evergreen Pharmaceuticals Co., Ltd., Lanzhou (CN)

( * ) Notice: Subject to any disclaimer, the term of this patent is extended or adjusted under 35 U.S.C. 154(b) by 569 days.

(21) Appl. No.: 17/996,226

(22) PCT Filed: Apr. 17, 2020

(86) PCT No.: PCT/CN2020/085383
§ 371 (c)(1),
(2) Date: Oct. 14, 2022

(87) PCT Pub. No.: WO2021/208080
PCT Pub. Date: Oct. 21, 2021

(65) Prior Publication Data
US 2023/0143813 A1    May 11, 2023

(51) Int. Cl.
*A61K 31/365* (2006.01)
*A61K 36/53* (2006.01)
*A61P 31/14* (2006.01)

(52) U.S. Cl.
CPC ............ *A61K 31/365* (2013.01); *A61K 36/53* (2013.01); *A61P 31/14* (2018.01); *A61K 2236/35* (2013.01); *A61K 2236/39* (2013.01)

(58) Field of Classification Search
CPC ........ A61K 31/365; A61P 31/14; A61P 11/00; A61P 31/12
See application file for complete search history.

(56) References Cited

PUBLICATIONS

Huang et al. Microbes and Infect. 2005, 7, 427-436 (Year: 2005).*
Liu et al. Nat. Sci. Rev. 2020, 7, 1003-1011 (Year: 2020).*
Wang et al. Eur. J. Pharmacol. 2017, 812, 9-17. (Year: 2017).*

* cited by examiner

*Primary Examiner* — Amanda L. Aguirre
(74) *Attorney, Agent, or Firm* — Hannah Tien

(57) ABSTRACT

A compound of Formula I compound—Ovatodiolide which is safe and effective to use in a pharmaceutical composition for inhibition of SARS-CoV-2 is provided. The pharmaceutical composition comprising a safe and effective amount of a compound of Formula I compound—Ovatodiolide or pharmaceutically acceptable salts thereof, together with a pharmaceutically acceptable carrier, which has great potential to treat SARS-CoV-2 induced COVID-19 based on a safe and effective amount of a compound of Formula I compound—Ovatodiolide.

8 Claims, 3 Drawing Sheets

USE OF OVATODIOLIDE AGAINST SARS-CoV-2

This application is a national stage application, filed under 35 U.S.C. § 371, of International Patent Application No. PCT/CN2020/085383, filed on Apr. 17, 2020, which is incorporated by reference herein in its entirety.

FIELD OF THE INVENTION

The focus of the present invention is a use of a Formula I compound—Ovatodiolide—Ovatodiolide (Ova) against SARS-CoV-2.

In the process of research and development, the preparation, identification, and analysis of a natural substance of the Formula I compound—Ovatodiolide, basic toxicological tests, simulations of molecular docking of the action mechanism of the Formula I compound—Ovatodiolide against the SARS-CoV-2, confirmations of the Formula I compound—Ovatodiolide against the SARS-CoV-2 by biochemical experiments, etc., are conducted and studied, and confirm sequentially that the Formula I compound—Ovatodiolide can be produced in an appropriate amount, is safe, and has an action mechanism and actual efficacy against the SARS-CoV-2; the Formula I compound—Ovatodiolide is indeed a natural substance that has a potential to inhibit infections of the SARS-CoV-2, and can be used for developing a medicine for preventing and treating the coronavirus disease 2019 (COVID-19).

BACKGROUND OF THE INVENTION

At present, as for SARS-CoV-2, no effective and preventive vaccines and no effective therapeutic medicines have been developed in the world; the SARS-CoV-2 has spread over all continents, leading to a global pandemic of the coronavirus disease. Many countries and cross-country pharmaceutical companies are actively conducting research and development of effective vaccines or medicines.

*Anisomeles indica* O. Kuntze is an herbal medicine commonly used in Taiwan, it is also known as "Hakka wipe grass" (Jiaoling, Meixian Guangdone), "golden sword grass", Ben Huoxiang, etc. The Ministry of Health and Welfare in Taiwan has included *Anisomeles indica* O. Kuntze in the List of raw materials that can be used in food, and the whole plant is edible. *Anisomeles indica* O. Kuntze is an annual or biennial herb of the Labiatae family. It is mainly distributed in southwestern China, India, the Philippines, Java and Sumatra of Indonesia. It can be found in the plains and low-altitude mountainous areas of Taiwan. There are also sporadic medicinal cultivations in Yuli, Hualien, Taiwan. For being used as medicine, it is harvested between summer and autumn, the whole grass is pulled up or the above ground part is cut off and collected, washed, and used fresh or sun-dried. The whole plant has effects of antipyretic, releasing colds, dehumidification, stomachic, detoxification, analgesic and antibacterial. It is commonly used for treating colds and fever, abdominal pain and vomiting, cholera, stomachache, gastroenteritis, neurodermatitis, rheumatism, muscle and bone pains, eczema, swollen poison, sores, stool poisoning, and poisonous snake bites.

The Research and Development Team has long been devoted to breeding *Anisomeles indica* O. Kuntze (GenBank: GU726292), and has been conducting a series of studies on the whole plant extract of *Anisomeles indica* O. Kuntze grown on farms, the focus is especially placed on the preparation of the crystalline pure substance of the Formula I compound—Ovatodiolide (FIG. 2), extraction, separation and purification, analysis and identification have been conducted, and anti-inflammation, anti-virus, anti-*Helicobacter pylori*, anti-cancer, anti-cancer stem cells and other pharmacological studies have also been carried out. In recent years, the Team has completed test experiments of the Formula I compound—Ovatodiolide in contrast to "Tamiflu" (Roche), a drug for the treatment of type A and type B influenza, and discovered that the compound of formula I—*Anisomeles indica* O. Kuntze extract and Ovatodiolide have an excellent effect on inhibiting influenza virus. It was recently discovered at the end of 2019 that AIDS drugs have shown positive responses for the treatment of patients with SARS-CoV-2 infections; according to literature reports, Ovatodiolide can inhibit HIV virus (Fitoterapia, 2000, 71(5): 574-576). In addition, current studies have also found that Ovatodiolide can inhibit gastritis caused by *Helicobacter pylori* in the gastric wall, and can also inhibit inflammatory responses mediated by NF-κB and STAT3, as a result, the Formula I compound—Ovatodiolide may also relieve the symptoms of pneumonia caused by the SARS-CoV-2.

DETAILED DESCRIPTION OF THE INVENTION

The present invention is based on the discovery that the Formula I compound—Ovatodiolide or pharmaceutically acceptable salts thereof can be used for inhibiting SARS-CoV-2 infection, even for treating or preventing SARS-CoV-2 pneumonia. Specifically, the present invention provides a pharmaceutical composition for inhibiting SARS-CoV-2 infection, even for treating or preventing pneumonia, which comprises a safe and effective amount of a Formula I compound—Ovatodiolide or pharmaceutically acceptable salts thereof, and a pharmaceutically acceptable carrier.

The present invention provides a pharmaceutical composition having a Formula I compound—Ovatodiolide as an effective component and mainly for inhibiting SARS-CoV-2 infections. The results of simulated molecular docking of the Formula I compound—Ovatodiolide to the receptor-binding domain (RBD) of spike glycoprotein on the surface of the SARS-CoV-2 show that: the Formula I compound—Ovatodiolide (Ova) binds to a hydrophobic pocket composed of several hydrophobic amino acids (L455, F456, Y489, F490) of the RBD, and forms hydrogen bonds with Y489 and Q493 (FIG. 3). The binding site is located at a joint where the SARS-CoV-2 spike glycoprotein RBD binds to human cell membrane receptor angiotensin-converting enzyme 2 (ACE2), which predicts that the Formula I compound—Ovatodiolide (Ova) can block or interfere with direct binding of the viral spike glycoprotein receptor-binding domain (RBD) to the receptor (ACE2). The binding of the SARS-CoV-2 surface spike glycoprotein to the human cell membrane receptor angiotensin-converting enzyme-2 (ACE2) is a key step of mediating virus invasion into a host, and blocking or interfering with the binding of the virus to the receptor is a potential prevention and treatment strategy.

The present invention provides a method for inhibiting severe acute respiratory syndrome coronavirus 2 (SARS-CoV-2), comprising administering a composition having a Formula I compound—Ovatodiolide as an effective component to a subject in need thereof.

At the same time, it is understood that the host endosomal cysteine proteolytic enzymes Cathepsin B and Cathepsin L play a key role in the fusion process of the SARS-CoV-2. The results of the simulated molecular docking also show that the Formula I compound—Ovatodiolide (Ova) may also bind to catalytic pockets of endosomal cysteine proteolytic enzymes Cathepsin B and Cathepsin L. and forms a covalent complex with catalytic cysteine C29 via an exocyclic olefin to inhibit the activity of Cathepsin B (FIG. 4A). On the other hand, the Formula I compound—Ovatodiolide (Ova) binds to a hydrophobic S2 site composed of L69, M70, Y72, A135, and M161 of Cathepsin L via a hydrophobic alicyclic ring, and forms a covalent complex with catalytic cysteine C25 via an exocyclic olefin to inhibit the activity of Cathepsin L (FIG. 4B). Since the endosomal cysteine proteolytic enzymes Cathepsin B and Cathepsin L play key roles in the fusion process of the SARS-CoV-2, the Formula I compound—Ovatodiolide (Ova) potentially blocks the invasive fusion process of the SARS-CoV-2.

This study specifically implements the SARS-CoV-2 pseudovirus inhibitory activity detection system developed by the laboratory of Professor Linqi Zhang, Director of the Comprehensive AIDS Research Center of Tsinghua University in Beijing, and specifically evaluates whether or not the Formula I compound—Ovatodiolide (Ova) blocks the process of infecting a host cell by the SARS-CoV-2. The experimental results show that, as for inhibition of coronavirus, the molecular action mechanism of the Formula I compound—Ovatodiolide is substantively different from that of chloroquine or Remdesivir, and the Formula I compound—Ovatodiolide exhibits an inhibitory effect on the SARS-CoV-2 infection significantly in the micromolar level (Figure. 5).

The Formula I compound—Ovatodiolide, can possess one or more chiral centers, and therefore have various stereoisomeric forms. The Formula I compound—Ovatodiolide described in the present invention includes all such isomers; in addition, it also includes derivative compounds comprising the main structure of the Formula I compound—Ovatodiolide, and, as for inhibition of SARS-CoV-2, the molecular action mechanism of these derivative compounds has an effect similar to the molecular docking mechanism of binding to the SARS-CoV-2 surface spike glycoprotein receptor-binding domain, or the molecular docking mechanism of binding to the host endosomal cysteine proteolytic enzymes Cathepsin B and Cathepsin L disclosed in the present invention. The Formula I compound—Ovatodiolide has the effect of selectively inhibiting SARS-CoV-2 infections; because of its extremely small molecular weight, lower doses of the Formula I compound—Ovatodiolide, or pharmaceutically acceptable salts thereof, and a pharmaceutically acceptable carrier can be used to obtain a desired therapeutic effect. The present invention is a pharmaceutical composition for inhibiting SARS-CoV-2 infections, even for treating or preventing coronavirus disease 2019 (COVID-19), wherein a safe and effective amount of the Formula I compound or pharmaceutically acceptable salts thereof and a pharmaceutical acceptable carrier is used for inhibiting SARS-CoV-2 infections, or is administered to a patient with symptoms of the coronavirus disease 2019 (COVID-19) to cure, restore, reduce, alleviate, alter, treat, ameliorate, improve or affect the disease, symptoms of the disease or physical conditions prone to be infected with the disease. As used herein, "an effective amount" refers to an effective amount of the Formula I compound—Ovatodiolide, or pharmaceutically acceptable salts thereof that has an inhibitory or therapeutic effect. The effective amount varies depending on the route of administration, excipient usage, and co-usage of other active ingredients.

As used herein, the "coronavirus disease 2019 (COVID-19)" refers to a deadly pneumonia caused by the invasion of severe acute respiratory syndrome coronavirus 2 (SARS-CoV-2) into a human body. The SARS-CoV-2 uses the spike glycoprotein on the surface of the coronavirus to identify angiotensin-converting enzyme-2 (ACE2) on the surface of a cell, and then infect normal cells of a human body. One possible mechanism is that when the virus invades the body, immune cells in the body react vigorously, an immune storm is triggered in the body to release a large number of free radicals (such as peroxide free radicals) to denature proteins, damage DNA, and over-produce cytokines, leading to serious cell necrosis, and developing severe and fatal pneumonia in the lungs. The Formula I compound—Ovatodiolide can effectively inhibit SARS-CoV-2 infections, which in turn prevents or treats coronavirus disease 2019 (COVID-19).

The Formula I compound—Ovatodiolide is prepared by extracting the whole plant, branches and leaves above ground, or leaves of *Anisomeles indica* O. Kuntze with an organic solvent, and then separating and purifying by a silica gel column; or prepared by chemical synthesis. For example: "*Anisomeles indica* O. Kuntze extract" refers to the *Anisomeles indica* O. Kuntze extract extracted from *Anisomeles indica* O. Kuntze of a suitable growth level. To obtain the *Anisomeles indica* O. Kuntze extract, extraction techniques well known in the art can be used. For example, dried and ground *Anisomeles indica* O. Kuntze can be suspended in a solvent or a mixture of two or more solvents for a sufficiently long period of time. Examples of suitable solvents include, but are not limited to, water, methanol, ethanol, acetone, ethers (for example, diethyl ether) and ethyl acetate and hexane. Then the solid residues are removed (for example, by filtration) to obtain the *Anisomeles indica* O. Kuntze extract solution, which can be purified by alumina, silica, silica gel column to obtain the Formula I compound—Ovatodiolide.

In a treatment method of the present invention, the Formula I compound—Ovatodiolide or its pharmaceutically acceptable salts can be administered simultaneously or separately, in the form of oral administration, non-oral administration, via inhalation spray or by means of an implanted reservoir. As used herein, "non-oral administration" refers to subcutaneous, intracutaneous, intravenous, intramuscular, intraarticular, intraarterial, intrasynovial, intrasternal, intrathecal, intralesional and intracranial injection and perfusion techniques. The Formula I compound—Ovatodiolide and/or its pharmaceutically acceptable salts used in the present invention can be combined with at least one solid, liquid, or semi-liquid excipient or adjuvant to form suitable pharmaceutical forms. The forms include, but are not limited to, lozenges, capsules, emulsions, aqueous suspensions, dispersions and solutions. Carriers commonly used for lozenges include lactose and cornstarch. A lubricating agent, such as magnesium stearate, is also typically added to the lozenge. Diluents used for capsule form include lactose and dried cornstarch. When an aqueous suspension or emulsion is used for oral administration, the active ingredients can be suspended or dissolved in an oily phase combined with an emulsifying or suspending agent. If desired, certain sweetening, flavoring and coloring agents may be added. The Formula I compound—Ovatodiolide or its pharmaceutically acceptable salts used in the present invention can also be formulated into sterile injectable components (e.g., aqueous or oily suspensions), for example, suitable dispersing or wetting agents (e.g., Tween 80) and suspending agents are used with techniques known in the art. Sterile injectable formulations can also be formed by incorporating sterile injectable solutions or suspensions into non-toxic non-oral diluents or solvents, such as 1,3-butanediol. Vehicles and solvents that can be used include mannitol, water, Ringer's solution and isotonic sodium chloride solution. In addition, sterile, fixed oils are often employed as solvent or suspending media (e.g., synthetic mono- or di-glycerides). Fatty acids such as oleic acid and its glyceride derivatives can also be used in the preparation of injectable agents, they are natural and pharmaceutically acceptable oils, for example, olive oil, castor oil, especially their polyoxyethylated variants. These oil solutions or suspensions may also include a long-chain alcohol diluent or dispersant, or carboxymethyl cellulose or similar dispersing agents. The Formula I compound—Ovatodiolide or pharmaceutically acceptable salts thereof used in the present invention can also be formulated into inhalation components according to techniques well known in the art. For example, salt solutions can be prepared by using benzyl alcohol or other suitable preservatives, adsorption promoters capable of enhancing bioavailability, fluorocarbon or other dissolving or dispersing agents well known in the art. Carriers used in the pharmaceutical composition must be "acceptable", compatible with the active ingredients of the formulation (and preferably capable of stabilizing the active ingredients) and causing no harms to patients. For example, solubilizers (e.g., cyclodextrins) (which form specific, more soluble complexes with one or more active compounds of the extract), serve as pharmacological adjuvants for the delivery of active ingredients. Examples of other carriers include colloidal silicon dioxide, magnesium stearate, cellulose and sodium lauryl sulfate.

In addition, when antiviral agents are administered in high doses, patients are easy to suffer from side effects. According to the results of a series of toxicological experiments of the Formula I compound—Ovatodiolide disclosed in the present invention, including single-dose oral acute toxicity tests of rats, 28-day feeding toxicity tests of rats, Ames tests of *Salmonella* reverse mutation, in vitro mammalian cell line chromosomal abnormality analysis tests, peripheral blood micronucleus tests of mice, etc., all show that the Formula I compound—Ovatodiolide has no genotoxicity, and provides a safe oral dose range. The pharmaceutical composition of the present invention comprises a safe and effective amount of the Formula I compound—Ovatodiolide, which is used for inhibiting SARS-CoV-2 infections, wherein the safe and effective amount for an average adult (60 kg of body weight) is less than 480 mg per day orally and is administered continuously for less than 28 days. Preferably, the safe and effective amount for an average adult (60 kg of body weight) is from 20 mg to 40 mg per day orally and is administered continuously for 7 to 14 days as appropriate. The specific dose administered to an individual patient depends on all possible factors, such as: activity of the specific compound used, age, body weight, general health conditions, gender, eating conditions, time and route of administration, excretion rate, drug substance combination, and the severity of the disease to be treated.

The present invention also provides a use of a composition for preparing a medicine for inhibiting coronavirus, wherein the composition comprises a Formula I compound—Ovatodiolide or a structural isomer of the Formula I compound—Ovatodiolide.

EMBODIMENTS

To make the above-described and other purposes, features, and advantages of the present invention more obvious and easier to understand, preferred embodiments are provided below, and are described in detail as follows:

Example 1. Preparation and Analysis of the Formula I Compound—Ovatodiolide

Figure 1:
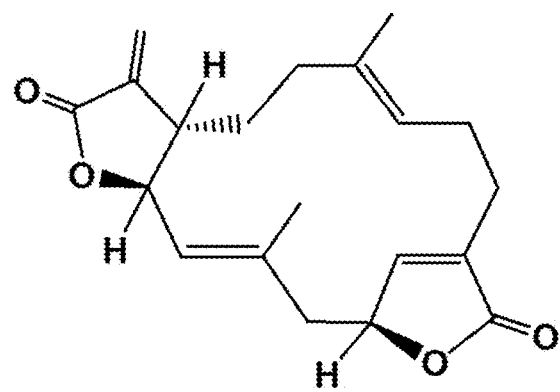
FIG. 1. The structure formula of the Formula I compound—Ovatodiolide.
Figure 2:
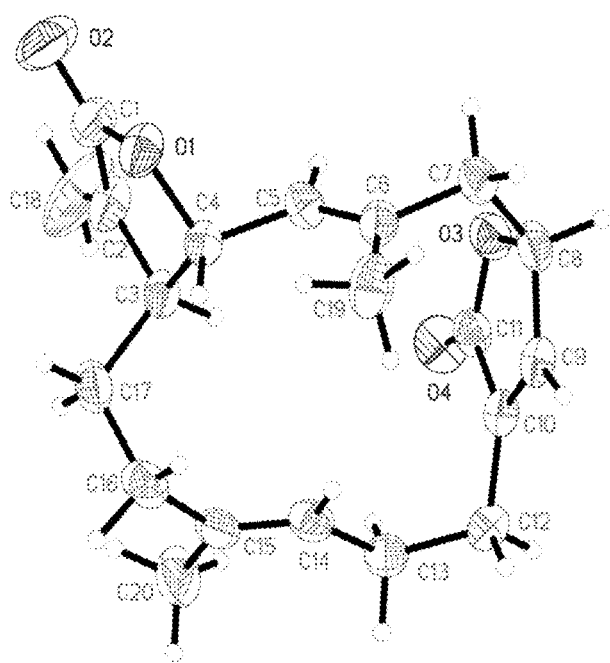
FIG. 2. The X-ray ORTEP diagram of the Formula I compound—Ovatodiolide crystal.

Roughly dried leaf part (800 g) of *Anisomeles indica* O. Kuntze (annual, harvested in autumn in Yuli, Hualien, Taiwan) was placed in a baking oven (40° C.) and dried (24 hours), to obtain dried leaves of *Anisomeles indica* O. Kuntze (500 g). The dried leaves of *Anisomeles indica* O. Kuntze (500 g) was placed in a 20-liter bucket (made of PE), and 10 liters of 95% alcohol was added to ensure that all the leaves were soaked in the solvent, then the bucket was sealed and stored in a cool place for 7 days. After 7 days, the 95% alcohol layer and the leaves were separated by filtration and concentrated by a rotary evaporation concentrator to obtain a yellow-green extract (10 g). Purification was carried out by alumia column chromatography (neutral aluminum oxide: 300 g). The yellow-green extract (10 g) was dissolved with 10 mL of acetone and added into an alumina-packed column. The solvent extraction ratio was Hexane:Ethyl acetate/100%:0%, and the polarity was gradually increased to Hexane:Ethyl acetate/70%:30%. After being screened and compared by using a thin-layer chromatography (TLC) paper test, the Formula I compound—Ovatodiolide flew out of the column in the third section. After volatile substances were dried by suction with a rotary evaporation concentrator, 15 mL of acetone was added to redissolve, then the solvent diffusion crystal growth method was used for 7 days to obtain 1.56 g of transparent crystal of the Formula I compound—Ovatodiolide, and the yield was about 0.3%. The purified crystals were confirmed to be the Formula I compound—Ovatodiolide. Through drying, extraction, purification and verification, we successfully isolated the Formula I compound—Ovatodiolide from Anisomeles indica O. Kuntze, and the yield of the leaves was about 3000 ppm. However, the leaves only accounted for less than 7% of the whole plant of Anisomeles indica O. Kuntze, and the collection was not easy. The Formula I compound—Ovatodiolide was analyzed and identified: X-ray Crystals of ovatodiolide were Orthorhombic, space group $P2_12_12_1$, with a=10.7714(3), b=12.8674(3), c=13.0829(3), V=1813.29(8) $Å^3$, D (calculated)=1.203 Mg/m3, Z=4, Formula weight=328.39, Goodness-of-fit on $F^2$=1.056, R indices (all data): R1=0.0347, wR2=0.0942. ORTEP diagram is depicted as FIG. 2. $^1$HNMR (400 MHz, $CDCl_3$): 1.59 (s, 3H), 1.62 (m, 1H), 1.64 (m, 1H), 1.72 (s, 3H), 2.04 (m, 1H), 2.12 (m, 1H), 2.19 (m, 1H), 2.26 (dd, 1H), 2.39 (m, 1H), 2.45 (m, 1H), 2.52 (m, 1H), 2.80 (m, 1H), 2.86 (dd, 1H), 4.81 (m, 1H), 4.85 (bd, 1H), 5.08 (m, 1H), 5.12 (bd, 1H), 5.57 (bs, 1H), 6.12 (bs, 1H), 6.98 (bs, 1H), $^{13}$CNMR (125 MHz, $CDCl_3$): 15.1, 19.3, 23.7, 24.9, 33.3, 36.3, 40.3, 42.7, 77.9, 78.8, 122.9, 125.0, 129.1, 131.2, 134.3, 134.5, 139.6, 147.4, 170.4, 173.0. FTIR (KBr pellet): 3100, 2900, 1740, 1650, 1430, 1395, 1320, 1200, 1110, 1045, 1080, 980, 960, 930, 910, 880, 860, 820, 750, 625 $cm^1$ and HRMS (ESI) m/z calcd. for $C_{20}H_{24}O_4$ (M+) 328.1675, found 328.1672.

Example 2. Single-Dose Oral Acute Toxicity Test of the Formula I Compound—Ovatodiolide in Rats This example was a single-dose oral acute toxicity safety test of the Formula I compound—Ovatodiolide in rats, and a reference for food safety assessment was provided. The test was conducted according to the guidelines such as the Taiwan Ministry of Health and Welfare Food Safety Assessment-Single-dose Oral Acute Toxicity Safety Test, the United States Environmental Protection Agency (USEPA) Health Effects Test Guidelines (OPPTS 870.1100, Acute oral toxicity, US EPA 712-C-98-190. In: OPPTS Harmonized Test Guidelines, Series 870.3050, EPA712-C-00-366) and the Organisation for Economic Co-operation and Development (OECD) Guidelines for the Testing of Chemicals (Section 4: Health Effects. No. 420: Acute Oral Toxicity-Fixed Dose Procedure, No 0.423: Acute Oral Toxicity-Acute Toxic Class Method, No. 425: Acute Oral Toxicity-Up and Down Method). In this experiment, single-dose oral acute toxicity tests of the Formula I compound—ovatodiolide were conducted in rats (Sprague-Dawley, S D strain). The Formula I compound—Ovatodiolide was in the form of yellowish crystals, the test purity was 99.95%, 10% of DMSO was used to prepare a solution concentration of 0.1 g/mL during the experiment, the feeding volume of each rat was 10 mL/kg body weight, the rats were fed orally based on their body weights on that day, the final dose was 1 g/kg-body weight in total, and the rats were continuously observed for 14 days after administration. The results showed that after the Formula I compound—Ovatodiolide was administered orally to rats, all the rats had no symptoms of being poisoned or died. In terms of weekly body weight changes (g), there was no significant difference in the weekly body weight and body weight gain of the male and female rats between the treatment group and the control group. After the tests, there was no significant abnormal changes in the blood values of the male and female rats in the treatment group, including: total white blood cells (WBC count), total red blood cells (RBC count), hematocrit (Hct), mean corpuscular volume (MCV), mean cell hemoglobin (MCH), mean cell hemoglobin concentration (MCHC), total platelets and leukocyte classification. No effects on the serum liver and kidney enzyme values of the male and female rats in the treatment group, including aspartate aminotransferase (AST), alanine aminotransferase (ALT), blood urea nitrogen (BUN), and creatinine, etc. There was no significant difference between the treatment group and the control group in absolute body weight (g) and organ weight percentage in adrenal gland, brain, heart, kidney, liver, spleen, thymus, testis, or ovary. After examination of internal organs, the adrenal gland, brain, heart, kidney, liver, spleen, thymus, testis or ovary and other important organs in the treatment group showed no pathological changes of any naked eyes. The results of histopathological examination showed that no histopathological changes in relation to the test substances was observed in important organs of the Formula I compound—Ovatodiolide treatment group. The comprehensive test results showed that no acute poisoning or death was caused in rats by the single-dose oral acute toxicity test of 1 g/Kg-body weight of the Formula I compound—Ovatodiolide (the equivalent human dose was about 50 mg/kg-body weight), and no pathological changes related to toxic reactions were caused to tissues or organs of the important organs in the body.

Example 3. 28-Day Feeding Toxicity Test of Formula I Compound—Ovatodiolide in Rats This example was a repeated dose oral toxicity safety test of the Formula I compound—Ovatodiolide in rats to establish a material safety data sheet, and a reference for clinical safety assessment of repeated administrations to human bodies was provided. The test was conducted according to the guidelines such as the Taiwan Ministry of Health and Welfare Food Safety Assessment 28-day Feeding Toxicity Test (1999) and Drugs Non-clinical Test Safety Guidelines (2014), and in compliance with the USEPA Health Effects Test Guidelines (OPPTS 870.1100, Repeated Dose 28-Day Oral Toxicity Study in Rodents. In: OPPTS Harmonized Test Guidelines, Series 870.3050, EPA712-C-00-366) and the OECD Guidelines for the Testing of Chemicals (Section 4: Health Effects. No. 407: Repeated Dose 28-day Oral Toxicity Study in Rodents). This experiment investigated whether the Formula I compound—Ovatodiolide might cause potential side effect toxicity to human bodies for clinical safety assessment, and 28-day repeated-dose oral toxicity tests of the Formula I compound—Ovatodiolide were conducted to observe clinical side effects. The Formula I compound—Ovatodiolide was a yellowish crystal, the test purity was regarded as 99.95%, and the samples were prepared with 5% of DMSO during the tests. Rats (Sprague-Dawley, S D strain) were divided into 4 groups, the control group (5% of DMSO), the low-dose group (10 mg/kg-body weight), the medium-dose group (25 mg/kg body weight) and the high-dose group (50 mg/kg-body weight), 20 rats in each group, half males and half females, each rat was fed with a volume of 10 mL/kg-body weight, and the rats were orally fed according to their body weight on the day for 28 consecutive days. The test results showed that after the Formula I compound—Ovatodialid was orally administered to the rats continuously for 28 days, no symptoms of being poisoned or death due to the test substance was observed in any rats. After the tests, the body weight changes, feed consumptions, urine, blood values, serum enzyme values and organ weights of the male and female rats in each Formula I compound—Ovatodiolide treatment group were compared to those of the control group, though slight increase or decrease due to individual difference were observed, they were within the normal range, no dose-response correlation was observed between the groups, there was no clinicopathological significance, and not related to the test substance. The organs in the entire body of the rats in each group were examined, there was no obvious pathological changes of any naked eyes, the results of histopathological examination showed that no pathological changes related to organ toxicity reaction was observed in each organ of the high-dose group. In view of the above test results, after the rats of the low-dose group (10 mg/kg-body weight), the medium-dose group (25 mg/kg-body weight) and the high-dose group (50 mg/kg-body weight) were orally fed respectively with the Formula I compound—Ovatodiolide for 28 days continuously, no toxic reactions was caused to various organs of the male and female rats, and the "No observed adverse effect level" (NOAEL) for the 28-day feeding toxicity test in rats was 50 mg/kg-body weight, the equivalent human dose was about 8 mg/kg-body weight.

Example 4. Ames Test of Formula I Compound-Ovatodiolide to *Salmonella* Reverse Mutation This example was the Ames tests of the Formula I compound—Ovatodiolide to reverse mutations of *Salmonella typhimurium* TA98, TA100, TA102, TA1535 and TA1537 strains to establish a Material Safety Data Sheet and provide a reference for use safety assessment. The tests were conducted according to the guidelines such as the Taiwan Ministry of Health and Welfare Genotoxicity study (1999) of the "Health Food Safety Assessment Method," the USEPA Health Effects Test Guidelines Bacterial Reverse Mutation Test (US EPA 712-C-98-247. In: OPPTS Harmonized Test Guidelines, Series 870.5100, 1998) and the OECD Guidelines for the Testing of Chemicals (Section 4: Health Effects. No. 471: Bacterial Reverse Mutation Test, 2002) to carry out the Ames tests. In this experiment, the Ames tests of the Formula I compound—Ovatodiolide to reverse mutations of the *Salmonella typhimurium* TA98, TA100, TA102, TA1535 and TA1537 strains were carried out. The Formula I compound—Ovatodiolide at concentrations of 1.25, 2.5 and 5 mg/plate, etc. were reacted with the strains for 18-20 hours to carry out the bacterial toxicity test. The results showed that when the concentration was 5 mg/plate or less, the Formula I compound—Ovatodiolide exhibited no significant toxicity to TA102 strain, but it was toxic to TA98, TA100, TA1535 and TA1537 strains; and then the bacterial toxicity tests were carried out by reacting the Formula I compound—Ovatodiolide with TA98, TA100, TA1535 and TA1537 for 18 hours at a concentration of 0.63, 1.25 and 2.5 mg/plate, respectively. The results showed that the Formula I compound—Ovatodiolide had no significant toxicity to TA98, TA100, TA1535 and TA1537 strains when the concentration was 2.5 mg/plate or less. The highest concentration of the Formula I compound—Ovatodiolide that exhibited no significant toxicity to TA102 strain was serially diluted down by 2 folds, and 5 concentrations of 0.31, 0.63, 1.25, 2.5 and 5 mg/plate were selected to conduct the formal Ames tests; and the highest concentration that exhibited no significant toxicity to TA98, TA100, TA1535 and TA1537 strains were serially diluted down by 2 folds, and 5 concentrations of 0.16, 0.31, 0.63, 1.25 and 2.5 mg/plate were selected to conduct the formal Ames test, the Formula I compound—Ovatodiolide acted directly, or after being mixed with rat liver activating enzyme extract (S9), on *Salmonella* mutant strains, it simulated the effect of the metabolites of the Formula I compound—Ovatodiolide, after being metabolized by the liver enzyme (S9) in the animal, on the gene mutation of each strain, and bacterial counts were conducted after co-cultivation for 48 hours. The results showed that the number of the reverse mutation bacteria was not more than 2 times of the number of reverse mutation bacteria in the negative control group, either the Formula I compound—Ovatodiolide acted directly or after being acted by S9. In view of the above results, the Formula I compound—Ovatodiolide exhibited no mutagenicity to *Salmonella* reverse mutations in the Ames tests, and the bacterial gene mutation test results were negative (non-genetic mutation in Ames test).

Example 5. In Vitro Mammalian Chromosome Aberration Analysis of Formula I Compound—Ovatodiolide This example was an in vitro mammalian chromosome aberration test of the Formula I compound—Ovatodiolide to establish a Material Safety Data Sheet and provide a reference for use safety assessment. The tests were conducted according to the Taiwan Ministry of Health and Welfare Health Food In vitro mammalian chromosome aberration analysis test and in compliance with the USEPA Health Effects Test Guidelines (OPPTS 870.1100, In vitro mammalian chromosome aberration test, US EPA 712-C-98-190. In: OPPTS Harmonized Test Guidelines, Series 870.3050, EPA712-C-00-366, 1998) and the OECD Guidelines for the Testing of Chemicals (Section 4: Health Effects. No. 473: In vitro mammalian chromosome aberration test 1997) to conduct genotoxicity tests. In this experiment, the chromosomal aberration test with mammalian cell in culture of the Formula I compound—Ovatodiolide was carried out. The Formula I compound—Ovatodiolide was yellowish crystals, and prepared with Dimethyl sulfoxide (DMSO) during the test. The cytotoxicity test was divided into two parts, in one part, CHO-K1 cells was reacted directly with the Formula I compound—Ovatodiolide, and in the other part, rat liver activating enzyme extract (S9) was used to simulate human metabolism, CHO-K1 cells, the rat liver activating enzyme extract (S9) and the Formula I compound—Ovatodiolide were mixed and then reacted. In the experiment that contained no rat liver activating enzyme extract (-S9), the cytotoxicity tests were conducted with 5 test doses of 12.5, 15, 17.5, 20 and 25 µM for 24 hours, and the results showed that when the Formula I compound—Ovatodiolide was 17.5 µM, the survival rate of the CHO-K1 cells was about 65.6%. In the experiment that contained the rat liver activating enzyme extract (+S9), the cytotoxicity tests were conducted with 5 test doses of 60, 70, 75, 80 and 90 µM for 24 hours, and the results showed that when the Formula I compound—Ovatodiolide was 75 µM, the survival rate of the CHO-K1 cells was about 60.3%, indicating that the Formula I compound—Ovatodiolide had cytotoxicity to the CHO-K1 cells, and this concentration was selected as the highest dose in the formal tests. For the chromosome aberration tests, the samples of the Formula I compound—Ovatodiolide were 12.5, 15 and 17.5 µM (-S9), the sample solutions were prepared in each cell culture plate, and co-cultivated for 24 hours; after 3 hours of co-cultivation with S9 at 55, 65 and 75 µM, the number and structure of the chromosomes in the cells were observed for 24 hours. The results showed that, under the test conditions that the Formula I compound—Ovatodiolide was mixed with or without the metabolic activation system of the S9 mixture solution, at 12.5, 15 and 17.5 µM (−S9) and 55, 65 and 75 µM (+S9), as compared to the negative control group, the frequency of chromosomal aberration in the CHO-K1 cells caused by three dose groups did not increase significantly, and there was no significant changes in the locations of cell chromosomal aberrations. In view of the above results, the Formula I compound—Ovatodiolide, containing the S9 mixture or not, had no mutagenic effect on the chromosomes of the in vitro mammalian cell line CHO-K1.

Example 6. Test of Formula I Compound-Ovatodiolide on Peripheral Blood Micronucleus in Mice This example was the genotoxicity test of the Formula I compound—Ovatodiolide to establish a Material Safety Data Sheet and provide a reference for use safety assessment. The tests were conducted according to guidelines such as the Taiwan Ministry of Health and Welfare Health Food Safety Assessment-Genotoxicity Test of Mice Peripheral Blood Micronucleus Test, and in compliance with the USEPA Mammalian Erythrocyte Micronucleus Test (In: OPPTS Harmonized Test Guidelines, Series 870.5395, EPA 712-C-98-226) and the OECD Guidelines for the Testing of Chemicals (Section 4: Health Effects. No. 474: Mammalian Erythrocyte Micronucleus Test, 1997) to conduct genotoxicity tests. In this experiment, the Formula I compound—Ovatodiolide on the peripheral blood micronucleus was tested in mice (ICR strain). This experiment mainly tested the effect of the Formula I compound—Ovatodiolide on the ratio of the occurrence of micronucleus in the peripheral blood of the mice (in vivo), so as to evaluate the level of damages caused by directly or indirectly triggered gene mutations of erythrocyte chromosomes or mitosis. ICR mice were used as the experimental subjects of this experiment, and the experiment was divided into 5 groups, the negative control group, the positive control group (Cyclophosphamide, 60 mg/kg bw ip), the Formula I compound—Ovatodiolide low dose (0.25 g/kg bw) group, the medium Dosage (0.5 g/kg bw) group and the high dose (1 g/kg bw) group, 5 mice (male) in each group, and Ovatodiolide was fed once by a gastric tube, 48 and 72 hours after the tested substances were administered, the reticulocytes and the occurrence (%) of micronucleus in the reticulocytes in the peripheral blood of the mice were evaluated. The results showed that 48 hours and 72 hours after the Formula I compound—Ovatodiolide was administered, no toxicity symptoms and no differences in the body weight were found in the treatment groups. The reticulocytes in the peripheral blood of the mice were stained with 0.1% of Acridine orange stain and orange-red color exhibited under a fluorescence microscope, yellow-green fluorescent micronuclei of about $1/20$-$1/5$ of the size of an erythrocyte were found in the reticulocytes. The number of reticulocytes and the number of micronuclei in the reticulocytes of each Formula I compound—Ovatodiolide treatment group at 48 hours and 72 hours were compared to those of the negative control group, there was no significant difference. The number of reticulocytes in the mice of the positive control group significantly decreased when compared to those of the negative control group ($p<0.05$), and the number of the micronuclei in the reticulocytes increased significantly ($p<0.05$). In view of the above results, when the number of reticulocytes and the micronuclei in the reticulocytes in the peripheral blood of the mice in each Formula I compound—Ovatodiolide dose group were compared to those of the negative control group, there was no significant difference, and the test results were negative. Therefore, the Formula I compound—Ovatodiolide in the peripheral erythrocytes of the mice had no toxic effect on chromosomal gene mutations.

Figure 3:
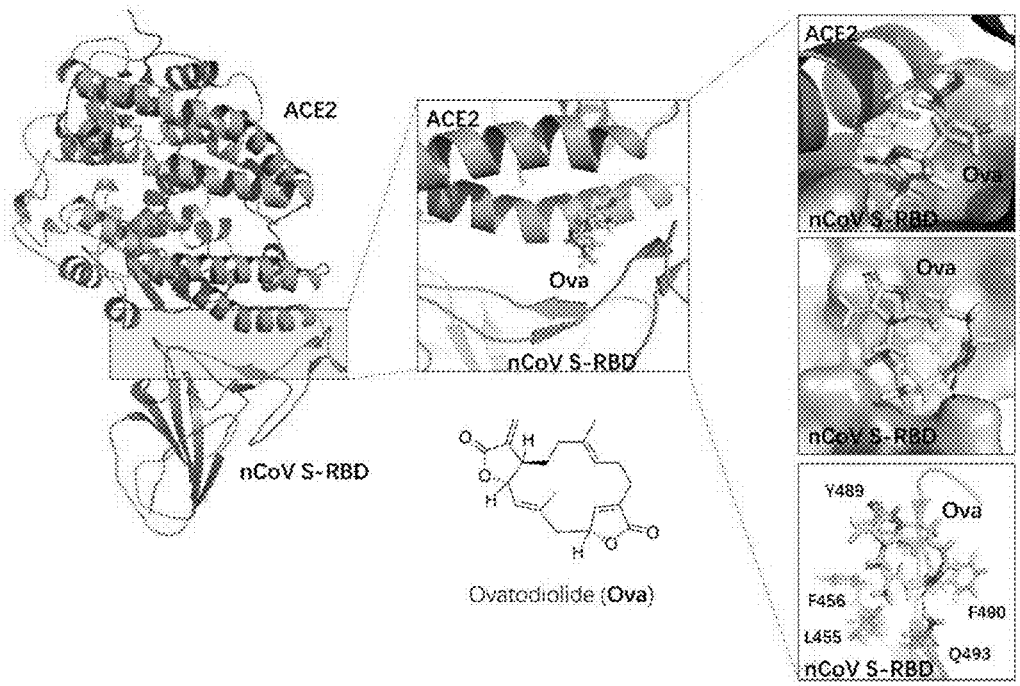
FIG. 3. The complex structure of the SARS-CoV-2 spike glycoprotein receptor-binding domain RBD and human cell membrane receptor ACE2, and the docking structure of the Formula I compound—Ovatodiolide (Ova) and RBD, the Formula I compound—Ovatodiolide (Ova) that binds to RBD and interferes with its binding to ACE2. The legends in the figure: ACE2: angiotensin-converting enzyme 2; nCov S-RBD: the SARS-CoV-2 spike glycoprotein receptor-binding domain; Ovatodiolide (Ova): the Formula I compound—Ovatodiolide.

Example 7. Molecular Docking Simulation Study Binding Formula I Compound—Ovatodiolide to SARS-CoV-2 Surface Spike Glycoprotein Receptor-Binding Domain The binding of SARS-CoV-2 surface spike glycoproteins with human cell membrane receptor angiotensin-converting enzyme 2 (ACE2) was a key step of mediating viral invasion into a host, and blocking or interfering with the binding of the virus with the receptor was a potential preventive and therapeutic strategy. This example intended to clarify the antiviral mechanism of the Formula I compound—Ovatodiolide, based on molecular dockings to evaluate whether or not the Formula I compound—Ovatodiolide (Ova) bound to the SARS-CoV-2 surface spike glycoprotein and blocked or interfered with its binding to the receptor molecule angiotensin-converting enzyme 2 (ACE2). The specific implementation method was as follows: the crystal structure (PDB code: 6M0J) of the spike glycoprotein receptor-binding domain (RBD) on the surface of the SARS-CoV-2 was used as a molecular docking receptor, and the MOE software was used to add hydrogen atoms to the RBD structure and perform energy optimization. The structure of the ligand Formula I compound—Ovatodiolide (Ova) was also constructed by using the MOE software, the standard MMFF94 molecular force field and the energy gradient of 0.0001 kcal/mol were used as the convergence criteria for energy optimization. Based on the molecular docking module of MOE was used to perform molecular dockings, and the energy-optimized docking structure was further subjected to energy optimization and docking mode analysis. The molecular docking results showed that the Formula I compound—Ovatodiolide (Ova) bound to a hydrophobic pocket composed of several hydrophobic amino acids (L455, F456, Y489, F490) of RBD, and formed hydrogen bonds with Y489 and Q493 (FIG. 3). The binding site was located at the joint where SARS-CoV-2 spike glycoprotein RBD bound to the receptor ACE2, it was predicted that the Formula I compound—Ovatodiolide (Ova) was able to block or interfere with direct binding between the virus spike glycoprotein RBD and the receptor ACE2.

Figure 4A:
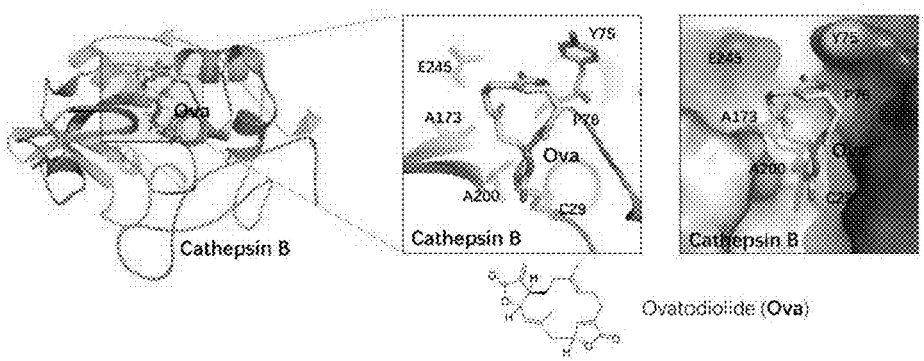
FIGS. 4A and 4B. The docking structure of the Formula I compound—Ovatodiolide (Ova) and cysteine proteolytic enzymes Cathepsin B (4A) and Cathepsin L (4B), wherein the Formula I compound—Ovatodiolide (Ova) forms covalent bonds with the catalytic cysteine C29 of Cathepsin B and the catalytic cysteine C25 of Cathepsin L by exocyclic alkene, respectively. The legends in the figure: Ovatodiolide (Ova): Formula I compound—Ovatodiolide; Cathepsin B: cysteine proteolytic enzyme B; Cathepsin L: cysteine proteolytic enzyme L.
Figure 4B:
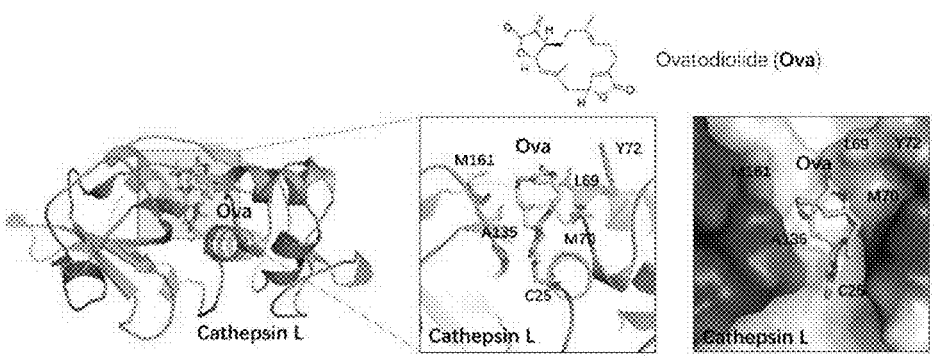

Example 8. Molecular Docking Simulation Study of Binding Formula I Compound—Ovatodiolide to Host Endosomal Cysteine Proteolytic Enzymes Cathepsin B and Cathepsin L The host endosomal cysteine proteolytic enzymes Cathepsin B and Cathepsin L played a key role in the fusion process of coronaviruses. Based on molecular dockings, this experiment evaluated whether or not the Formula I compound—Ovatodiolide bound and inhibited Cathepsin B and Cathepsin L to explain the antiviral mechanism of the Formula I compound—Ovatodiolide. The method of the example was as follows: the crystal structures of the human endosomal cysteine proteolytic enzymes Cathepsin B and cathepsin L (PDB code: 3AI8 & 2XU1) were respectively used as molecular docking receptors, and the MOE software was used to add hydrogen atoms to the RBD structure and to carry out energy optimization. The structure of the ligand Formula I compound—Ovatodiolide (Ova) was also constructed by using the MOE software, the standard MMFF94 molecular force field and the energy gradient of 0.0001 kcal/mol were used as the convergence criteria for energy optimization. Based on the molecular docking module of MOE performed molecular docking, and the energy-optimized docking structure further performed energy optimization and docking mode analysis. The molecular docking results showed that the Formula I compound—Ovatodiolide (Ova) might also bind to the catalytic pockets of the endosomal cysteine proteolytic enzymes Cathepsin B and Cathepsin L. The Formula I compound—Ovatodiolide (Ova) bound to a hydrophobic S2 site, composed of Y75, P76, A173, A200, and E245, of Cathepsin B via a hydrophobic alicyclic ring, and formed a covalent complex with the catalytic cysteine C29 via exocyclic olefin to inhibit the activity of Cathepsin B (FIG. 4A). On the other hand, the Formula I compound—Ovatodiolide (Ova) bound to a hydrophobic S2 site, composed of L69, M70, Y72, A135, and M161, of Cathepsin L via a hydrophobic alicyclic ring, and formed a covalent complex with the catalytic cysteine C22 via exocyclic olefin to inhibit the activity of Cathepsin L (FIG. 4B). Since the endosomal cysteine proteolytic enzymes Cathepsin B and Cathepsin L played a key role in the fusion process of coronaviruses, the Formula I compound—Ovatodiolide (Ova) potentially blocked the process of invasion and fusion of the SARS-CoV-2.

Figure 5:
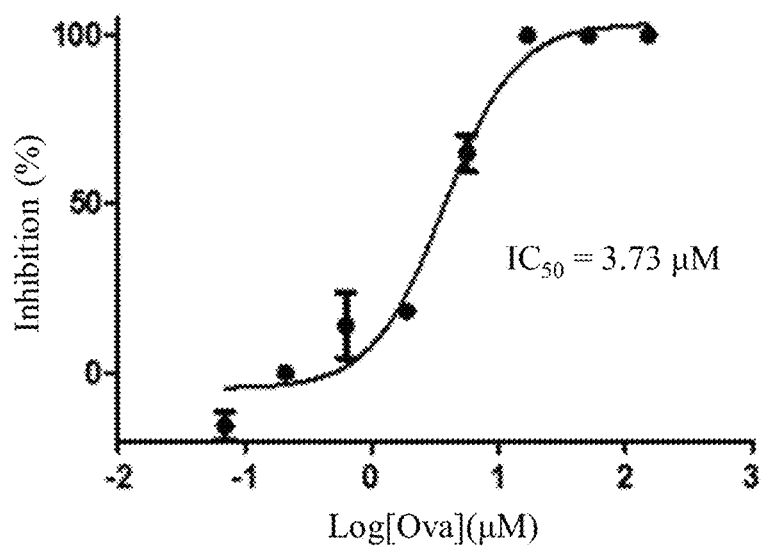
FIG. 5. It is the activity curve of the Formula I compound—Ovatodiolide for inhibiting SARS-CoV-2 infections, $IC_{50}=3.73$ μM.

Example 9. Study of the Activity of Formula I Compound-Ovatodiolide on Inhibiting SARS-CoV-2 Infections The research results of the simulated molecular docking of the Formula I compound—Ovatodiolide and the SARS-CoV-2 surface spike glycoprotein receptor-binding domain (RBD) described in Example 7, and the research results of the simulated molecular docking of the Formula I compound—Ovatodiolide and the endosomal cysteine proteolytic enzymes Cathepsin B and Cathepsin L, etc., described in Example 8 predicted that the Formula I compound—Ovatodiolide could inhibit the infection process of the SARS-CoV-2. This example evaluated whether or not the Formula I compound—Ovatodiolide blocked the process of infecting a host cell by the SARS-CoV-2, based on the SARS-CoV-2 pseudovirus inhibitory activity detection system developed by the laboratory of Professor Linqi Zhang, Director of the Comprehensive AIDS Research Center of Tsinghua University, Beijing. The method of the example was carried out according to two steps of constructing SARS-CoV-2 pseudovirus and testing the inhibition of SARS-CoV-2 infections: Step 1. membrane glycoprotein deletion (Env-defective) and HIV-1 virus genome plasmid pNL4-3R-E-luciferase expressing fluorescein protein, and co-transfected 293T cells expressing the SARS-CoV-2 full-length surface spike glycoprotein plasmid pcDNA3.1/SARS-CoV-2 were used and cultivated in DMEM medium containing 10% fetal bovine serum for 60 hours. The culture supernatant was harvested to obtain a virus solution of the SARS-CoV-2 pseudovirus (herein referred to as SARS-CoV-2 virus solution). Step 2. A 96-well cell culture plate was used, 100 microliters of the Formula I compound—Ovatodiolide diluent and 50 microliters of SARS-CoV-2 virus solution (the virus concentration in 50 microliters of SARS-CoV-2 virus solution was $1\times10^4$ TCID50/mL) were added to each well, so that the concentration of the Formula I compound—Ovatodiolide solution in the mixture system was the corresponding dilution concentration, and incubated at 37° C. for 1 hour. An equal volume of DMEM medium containing 10% fetal bovine serum was used to replace the dilution of the Formula I compound—Ovatodiolide solution as the virus control. An equal volume of DMEM medium containing 10% of fetal bovine serum was used to replace the SARS-CoV-2 virus solution as the cell control. The described cell culture plate was used, and 100 microliters of Huh7 cell suspension (the solvent used for preparing the cell suspension was DMEM medium containing 10% of fetal bovine serum, and the concentration of Huh7 cells in the cell suspension was $2\times10^5$ cells/mL) was seeded in each well, stood and incubated at 37° C. for 64 hours. The supernatant was discarded, 150 microliters of lysis solution (Microglass Biotechnology, Product number T003, operated according to the instructions) was added to each well, stood and incubated at 37° C. for 5 minutes. A cell culture plate was used, and the luciferase activity was examined. Multiple replicate wells were set up for each treatment. Inhibitory activity (%)=[1−(fluorescence intensity of the test group−fluorescence intensity of the cell control)/(fluorescence intensity of the virus control−fluorescence intensity of the cell control)]×100%. Prism 5 software was used to calculate the concentration of the Formula I compound—Ovatodiolide when the inhibitory activity was 50%, i.e., the $IC_{50}$ value of the Formula I compound—Ovatodiolide (FIG. 5). The research results showed that the Formula I compound—Ovatodiolide had a molecular mechanism of inhibiting the SARS-CoV-2 that was different from that of chloroquine or Remdesivir, and exhibited a significant inhibitory effect on coronavirus infections at the micromolar level.

What is claimed is:

1. A method for inhibiting severe acute respiratory syndrome coronavirus 2 (SARS-CoV-2) which comprises administering a safe and effective amount of Formula I compound—Ovatodiolide or a safe and effective amount of structural isomer of the Formula I compound—Ovatodiolide to a subject, Formula I 2. The method of claim 1, wherein the safe and effective amount of the Formula I compound—Ovatodiolide or the safe and effective amount of structural isomer of the Formula I compound—Ovatodiolide is combined with a pharmaceutically acceptable salt thereof or a carrier to form a composition.

3. The method of claim 2, wherein the composition can be used for preventing or treating diseases caused by SARS-CoV-2.

4. The method of claim 2, wherein the composition can be used for preventing or treating coronavirus disease 2019 (COVID-19).

5. The method of claim 1, wherein the Formula I compound—Ovatodiolide is a natural compound as a component prepared by extracting *Anisomeles indica* D. Kuntze with an organic solvent and separating and purifying by a chromatographic column, or is a synthetic compound having the same structure as the natural Formula I compound—Ovatodiolide as a component prepared by chemical synthesis.

6. The method of claim 2, wherein the safe and effective amount for an adult with body weight of 60 kg is less than 480 mg per day orally, and administered continuously for less than 28 days.

7. The method of claim 2, wherein the safe and effective amount for an adult with body weight of 60 kg is from 20 mg to 40 mg per day orally, and administered continuously for 7 to 14 days as appropriate.

8. A method for inhibiting coronavirus which comprises administering a safe and effective amount of Formula I compound—Ovatodiolide, or a safe and effective amount of structural isomer of the Formula I compound—Ovatodiolide to a subject.

* * * * *